United States Patent [19]
Capaldi et al.

[11] Patent Number: 6,020,475
[45] Date of Patent: Feb. 1, 2000

[54] PROCESS FOR THE SYNTHESIS OF OLIGOMERIC COMPOUNDS

[75] Inventors: Daniel C. Capaldi, San Diego; Vasulinga T. Ravikumar, Carlsbad, both of Calif.

[73] Assignee: Isis Pharmeuticals, Inc., Carlsbad, Calif.

[21] Appl. No.: 09/021,277

[22] Filed: Feb. 10, 1998

[51] Int. Cl.$^7$ .............................. C07H 21/02; C07H 21/04
[52] U.S. Cl. ...................... 536/23.1; 536/24.3; 536/24.5; 536/26.7; 536/25.34
[58] Field of Search ................................ 536/23.1, 24.3, 536/24.5, 26.7, 25.34

[56] References Cited

U.S. PATENT DOCUMENTS

| | | | |
|---|---|---|---|
| Re. 34,069 | 9/1992 | Köster | 536/25.34 |
| 3,687,808 | 8/1972 | Merigan et al. | 435/91.3 |
| 4,415,732 | 11/1983 | Caruthers et al. | 536/26.5 |
| 4,458,066 | 7/1984 | Caruthers et al. | 536/25.34 |
| 4,500,707 | 2/1985 | Caruthers et al. | 536/25.34 |
| 4,668,777 | 5/1987 | Caruthers et al. | 536/26.5 |
| 4,725,677 | 2/1988 | Köster et al. | 536/25.34 |
| 4,816,571 | 3/1989 | Andrus et al. | 536/25.3 |
| 4,973,679 | 11/1990 | Caruthers et al. | 536/26.71 |
| 5,026,838 | 6/1991 | Nojiri et al. | 536/25.34 |
| 5,132,418 | 7/1992 | Caruthers et al. | 536/25.3 |
| 5,185,334 | 2/1993 | Solomon et al. | 514/236.2 |
| 5,210,264 | 5/1993 | Yau | 558/167 |
| 5,212,295 | 5/1993 | Cook | 536/26.7 |
| 5,527,899 | 6/1996 | Froehler | 536/25.3 |
| 5,554,746 | 9/1996 | Ravikumar et al. | 540/200 |
| 5,571,902 | 11/1996 | Ravikumar et al. | 536/22.1 |
| 5,705,621 | 1/1998 | Ravikumar | 536/23.1 |
| 5,714,597 | 2/1998 | Ravikumar et al. | 536/25.31 |
| 5,760,209 | 6/1998 | Cheruvallah et al. | 536/25.34 |
| 5,783,690 | 7/1998 | Cheruvallah et al. | 536/55.3 |

FOREIGN PATENT DOCUMENTS

| | | |
|---|---|---|
| 0 506 242 A1 | 3/1992 | European Pat. Off. |
| 9113080 | 9/1991 | WIPO |
| 9205180 | 4/1992 | WIPO |
| 9719092 | 5/1997 | WIPO |
| 9829429 | 7/1998 | WIPO |

OTHER PUBLICATIONS

Watanabe et al., "Utilization of O–Xylylene N, N–Diethylphosphoramidite for the Synthesis of Phosphoric Diesters," *Tetrahedron Letters*, 33(10), 1313–1316 (Mar. 3, 1992).

Andrade et al., "Efforts Toward Synthesis of Oligonucleotides for Commercialization," *Nucleosides & Nucleotides*, 16(7–9), 1617–1620 (Sep. 15, 1996).

Cheruvallah et al.(III), "Solution Phase Synthesis of an Oligodeoxyribonucleotide Phosphorthioate for Therapeutic Applications," *Nucleosides & Nucleotides*, 16(7–9), 1625–1628 (Sep. 15, 1996).

Krotz et al., "Improved Impurity Profile of Phosphorothioate Oligonucleotides Through the Use of Dimeric Phosphoramidite Synthons," *Nucleosides & Nucleotides*, 16(7–9), 1637–1640 (Sep. 15, 1996).

Agrawal, S., Eds., *Protocols for Oligonucleotides and Analogs*, 1993, Humana Press, Totowa, NJ.

Alul, R.H. et al., "Oxalyl–CPG: a labile support for synthesis of sensitive oligonucleotide derivatives", *Nuc. Acid Res.*, 1991, 19, 1527–1532 (No. 7).

Ausubel, F.M. et al., Eds., *Current Protocols in Molecular Biology*, 1993, Current Publications.

Bannwarth, W., "Synthesis of Oligodeoxynucleotides by the Phosphite–Triester Method Using Dimer Units and Different Phosphorous–Protecting Groups", *Helvetica Chim. Acta*, 1985, 68, 1907–1913.

Beaucage, S.L. et al., "Advances in the Synthesis of Oligonucleotides by the Phosphoramidite Approach", *Tetrahedron*, 1992, 48, 2223–2311 (No. 12).

Bielinska, A. et al., "Regulation of Gene Expression with Double–Stranded Phosphorothioate Oligonucleotides", *Science*, 1990, 250, 997–1000 (Nov. 16, 1990).

Brown, T. et al., "Modern machine–aided methods of oligodeoxyribonucleotide synthesis", *Oligonucleotides and Analogs*, Ekstein, F., eds., IRL Press, Oxford, 1–24.

Cook, P.D., "Medicinal chemistry of antisense oligonucleotides—future opportunities", *Anti–Cancer Drug Design*, 1991, 6, 585–607.

Delgado, C. et al., "The Uses and Properties of PEG–Linked Proteins", *Crit. Rev. in Therapeutic Drug Carrier Sys.*, 1992, 9, 249–304.

Efimov, V.A. et al., "New efficient sulfurizing reagents for the preparation of oligodeoxyribonucleotide phosphorothioate analogues", *Nucl. Acids. Res.*, 1995, 23, 4029–4033 (Issue No. 20).

Englisch, U. et al., "Chemically Modified Oligonucleotides as Probes and Inhibitors", *Angew. Chem. Int. Ed. Eng.*, 1991, 30, 613–629, No. 6, Jun. 1991.

Greene et al., *Protective Groups in Organic Synthesis*, 1991, 2nd Ed., John Wiley & Sons.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

Iyer, R.P. et al., "The Automated Synthesis of Sulfur–Containing Oligodeoxyribonucleotides Using 3H–1, 2–Benzodithiol–3–one 1,1–Dioxide as Sulfur–Transfer Reagent", *J. Org. Chem.*, 1990, 55, 4693–4699, No. 15.

(List continued on next page.)

*Primary Examiner*—L. Eric Crane
*Attorney, Agent, or Firm*—Woodcock Washburn Kurtz Mackiewicz & Norris LLP

[57] ABSTRACT

Synthetic processes are provided wherein oligomeric compounds are prepared having phosphodiester, phosphorothioate, and phosphorodithioate covalent linkages. Also provided are synthetic intermediates useful in such processes.

62 Claims, No Drawings

OTHER PUBLICATIONS

Kamer, P.C.J. et al., "An Efficient Approach Toward the Synthesis of Phosphorothioate Diesters via the Schonberg Reaction", *Tetrahedron Letts.*, 1989, 30, 6757–6760, No. 48.

Kroschwitz, J.I., "Polynucleotides", *Concise Encyclopedia of Polymer Science and Engineering*, 1990, John Wiley & Sons, New York, 858–859.

Kumar, G. et al., "Improvements in Oligodeoxyribonucleotide Synthesis: Methyl N,N–Dialkylphosphoramidite Dimer Units for Solid Support Phosphite Methodology", *J. Org. Chem.*, 1984, 49, 4905–4912, No. 25.

Miura, K. et al., "Blockwise Mechanical Synthesis of Oligonucleotides by the Phosphoramidite Method", *Chem. Pharm. Bull.*, 1987, 35, 833–836, No. 2.

Ouchi, T. et al., "Synthesis and Antitumor Activity of Poly(Ethylene Glycol)s Linked to 5'–Fluorouracil via a Urethane or Urea Bond", *Drug Des. & Disc.*, 1992, 9, 93–105.

Pierce, M.E. et al., "Stereoselective Synthesis of HIV–1 Protease Inhibitor, DMP 323", *J. Org. Chem.*, 1996, 61, 444–450, No. 2.

Rao, M.V. et al., "Dibenzoyl Tetrasulphide—A Rapid Sulphur Transfer Agent in the Synthesis of Phosphorothioate Analogues of Oligonucleotides", *Tetrahedron Letts.*, 1992, 33, 4839–4842, No. 33.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.*, 1991, 56, 4329–4333, No. 13.

Sambrook, J. et al., Eds., *Molecular Cloning, A Laboratory Manual*, 1989, 2nd Ed., Cold Spring Harbor Laboratory Press.

Sanghvi, *Antisense Research and Application*, 1993, Ch. 15, Crooke, S.T. et al., Eds., CRC Press.

Secrist, J.A. et al., "Synthesis and Biological Activity of 4'–Thionucleosides", *10th International Rountable: Nucleosides, Nucleotides and their Biological Applications*, Sep. 16–20 1985, Abstract 21, Park City, Utah, 40.

Stec, W.J. et al., "Stereospecific Synthesis of P–chiral Analogs of oligonucleotides", *Methods in Molecular Biology*, 20, 1993, Chapter 14, Humana Press, Totowa, NJ, 285–313.

Stec, W.J. et al., "Novel route to oligo(deoxyribonucleoside phosphorothioates). Stereocontrolled synthesis of P–chiral oligo(deoxyribonucleoside phosphorothioates)", *Nucl. Acids Res.*, 1991, 19, 5883–5888, No. 21.

Stec et al., "Bis (O,O–Diisopropoxy Phosphinothioyl)Disulfide—A Highly Efficient Sulfurizing Reagent for Cost–Effective Synthesis of Oligo(Nucleoside Phosphorothioate)s", *Tetrahedron Letts.*, 1993, 34, 5317–5320, No. 33.

Vu, H., "Internucleotide Phosphite Sulfurization with Tetraethyl Thiuram Disulfide. Phosphorothioate Oligonucleotide Synthesis via Phosphoramidite Chemistry", *Tetrahedron Letts.*, 1991, 32, 3005–3008, No. 26.

Wolter, A. et al., Polymer Support Oligonucleotide Synthesis XX: Synthesis of a Henhectacosa Deoxynucleotide by use of a Dimeric Phosphoramidite *Nucleosides & Nucleotides*, 1986, 5, 65–77.

Wright, P. et al., "Large Scale Synthesis of Oligonucleotides bia Phosphora;midite Nulceosides and a High–loaded Poylstyrene Support", *Tetrahedron Letts.*, 1993, 34, 3373–3376, No. 21.

Wu, H. et al., "Inhibition of in vitro transcription by specific double–stranded oligodeoxyribonucleotides", *Gene*, 1990, 89, 203–209.

Xu, Q. et al., "Use of 1,2,4–dithiazolidine (DtsNH) and 3–ethoxy–1,2,4–dithiazoline–5–one (EDITH) for synthesis of phosphorothioate–containing oligodeoxyribonucleotides", *Nucl. Acids Res.*, 1996, 24, 1602–1607, No. 9.

Xu, Q. et al., "Efficient introduction of phosphorothioates into RNA oligonucleotides by 3–ethoxy–1,2,4–dithiazoline–5–one (EDITH)", *Nucl. Acids Res.*, 1996, 24, 3643–3644, No. 18.

Aldrich Chemical Company Catalog, 1994–1995, p. 32.

PROCESS FOR THE SYNTHESIS OF OLIGOMERIC COMPOUNDS

FIELD OF THE INVENTION

This invention relates to methods for the preparation of oligomeric compounds having phosphite, phosphodiester, phosphorothioate, phosphorodithioate or other linkages, and to intermediates useful in their preparation.

BACKGROUND OF THE INVENTION

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomeric compounds to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous processes for coupling nucleosides through phosphorous-containing covalent linkages to produce oligonucleotides of defined sequence. One of the most popular processes is the phosphoramidite technique (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

The phosphoramidite technique, however, has significant disadvantages. For example, cyanoethyl phosphoramidite monomers are quite expensive. Although considerable quantities of monomer go unreacted in a typical phosphoramidite coupling, unreacted monomer can be recovered, if at all, only with great difficulty.

Another disadvantage of using a β-eliminating cyanoethoxy group is formation of acrylonitrile upon removal of the phosphorus protecting group. Acrylonitrile is a highly toxic agent as well as a suspected carcinogen (See 1994–1995 Aldrich Chemical Company Catalog, at page 32). Acrylonitrile is also suspected of forming cyclic structures with thymidine resulting in oligomeric compounds having decreased hybridization ability. These modified oligomeric compounds are undesirable because they are difficult to separate from the desired oligomeric compound.

Consequently, there remains a need in the art for synthetic methods that will overcome these problems.

Several processes are known for the solid phase synthesis of oligonucleotide compounds. These are generally disclosed in the following U.S. Pat. No. 4,458,066; issued Jul. 3, 1984; No. 4,500,707, issued Feb. 19, 1985; and No. 5,132,418, issued Jul. 21, 1992. Additionally, a process for the preparation of oligonucleotides using phosphoramidite intermediates is disclosed in U.S. Pat. No. 4,973,679, issued Nov. 27, 1990.

A process for the preparation of phosphoramidites is disclosed in U.S. Pat. No. 4,415,732, issued Nov. 15, 1983.

Phosphoramidite nucleoside compounds are disclosed in U.S. Pat. No. 4,668,777, issued May 26, 1987.

A process for the preparation of oligonucleotides using a β-eliminating phosphorus protecting group is disclosed in U.S. Pat. No. Re. 34,069, issued Sep. 15, 1992.

A process for the preparation of oligonucleotides using a β-eliminating or allylic phosphorus protecting group is disclosed in U.S. Pat. No. 5,026,838, issued Jun. 25, 1991.

SUMMARY OF THE INVENTION

It is an object of the present invention to provide methods for the preparation of oligomeric compounds having phosphite, phosphodiester, phosphorothioate, phosphorodithioate, or other phosphorus-containing covalent linkages.

It is a further object of the present invention to provide synthetic intermediates useful in such processes. Other objects will be apparent to those skilled in the art.

These objects are satisfied by the present invention, which provides methods for the preparation of oligomeric compounds having phosphite, phosphodiester, phosphorothioate, or phosphorodithioate containing covalent linkages.

In one aspect of the present invention, methods are provided for the preparation of oligomeric compounds comprising a moiety having the Formula I:

wherein:
$X_4$ is Z or H;
Z is CN, halogen, $NO_2$, alkaryl, sulfoxyl, sulfonyl, thio, substituted sulfoxyl, substituted sulfonyl, or substituted thio, wherein said substituent is alkyl, aryl, or alkaryl;
$X_1$ is O or S;

comprising:

(a) providing a compound having the Formula II:

wherein:
each $R_1$, is, independently, H, —OH, —F, or —O—$X_3$—D;
 $X_3$ is alkyl having from 1 to 10 carbons;
 D is H, amino, protected amino, alkyl substituted amino, imidazole, or (—O—$X_3$)$_p$, where p is 1 to about 10;
each $X_2$ is O or S;
$R_3$ is hydrogen, a hydroxyl protecting group, or a linker connected to a solid support;
each B, independently, is a naturally occurring or non-naturally occurring nucleobase or a protected naturally occurring or non-naturally occurring nucleobase;
n is 0 to about 50;
each Q is —$X_1$H or $R_5$ is —N($R_6$)$_2$, or a heterocycloalkyl or heterocycloalkenyl ring containing from 4 to 7 atoms, and having up to 3 heteroatoms selected from nitrogen, sulfur, and oxygen; and
$R_6$ is straight or branched chain alkyl having from 1 to 10 carbons; and (b) reacting the compound of Formula II with a compound having Formula III:

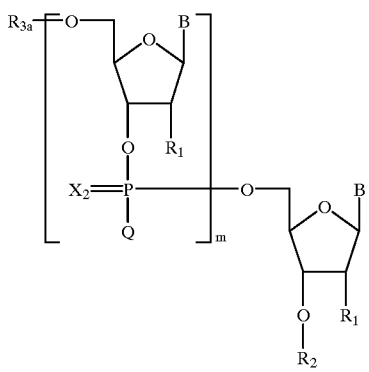

III

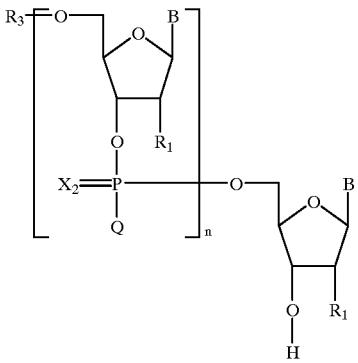

V wherein m is 0 to about 50; $R_{3a}$ is hydrogen; and $R_2$ is a hydroxyl protecting group, or a linker connected to a solid support, provided that $R_2$ and $R_3$ are not both simultaneously a linker connected to a solid support; to form the oligomeric compound.

Some preferred embodiments of the methods of the invention further comprise the step of oxidizing or sulfurizing the oligomeric compound. In some preferred embodiments, the methods of the invention further comprise transforming the oxidized or sulfurized oligomeric compound to form a further compound having the Formula III, where m is increased by 1.

In some preferred embodiments, the moiety —CH($X_4$)—Z is in the ortho or para position of the phenyl ring, with the para position being especially preferred.

Preferably, the methods of the invention comprise a capping step, either prior to or after the oxidation step.

Other preferred embodiments of the invention further comprise the step of cleaving the oligomeric compound to produce a compound having the Formula IV:

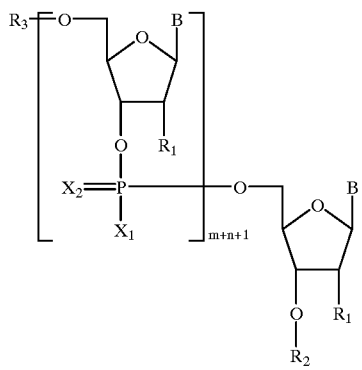

IV

In some preferred embodiments of the invention, Z is CN. In particularly preferred embodiments, $X_4$ is H, and the moiety —CH ($X_4$)—Z is in the para position.

In further preferred embodiments of the invention, each $R_6$ is isopropyl. In other preferred embodiments, $X_1$ and $X_2$ are each independently O or S.

In some preferred embodiments the compound of Formula II is obtained by reaction of a compound having the Formula V:

with a compound having the Formula VI:

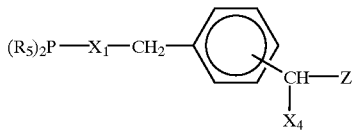

VI in the presence of an acid, preferably wherein —CH($X_4$)—Z is in the ortho or para position. Preferably, $R_5$ is N,N-diisopropylamino.

In other preferred embodiments, the compound of Formula II is obtained by reacting a protected nucleoside with a chlorophosphine of formula $ClP[i-Pr_2N]_2$, followed by reaction with a compound of formula:

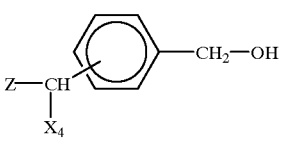

preferably wherein —CH ($X_4$)—Z is in the ortho or para position.

Also provided in accordance with the present invention are methods for the preparation of a protected nucleoside phosphoramidite of formula:

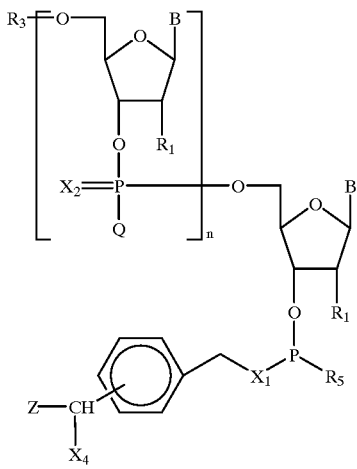

wherein:

X₄, Z, X₁, R₁, X₂, R₃, B, n, Q and R₅ are defined as above; comprising:

selecting a protected nucleoside of formula V:

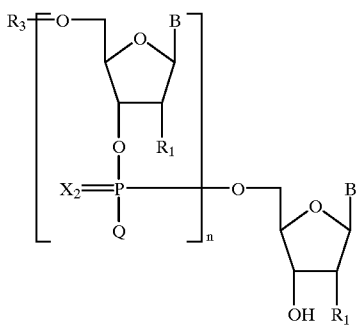

reacting the protected nucleoside with a chlorophosphine compound of formula ClP(R₅)₂ in the presence of a base; and protecting the product by reaction with a compound of Formula XX:

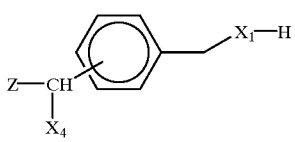

in the presence of an acid;

to form the protected nucleoside phosphoramidite.

In some preferred embodiments, Z is CN. In further preferred embodiments X₄ is H. In still further preferered embodiments X₁ is O.

Also provided in accordance with the invention are novel compounds having the Formula VII:

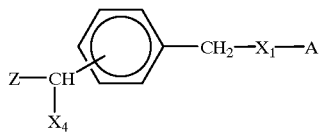

wherein:

$X_1$ is O or S;

A is H or $(R_7)(R_8)$ P;

$R_8$ is $R_5$, or has the Formula VIII:

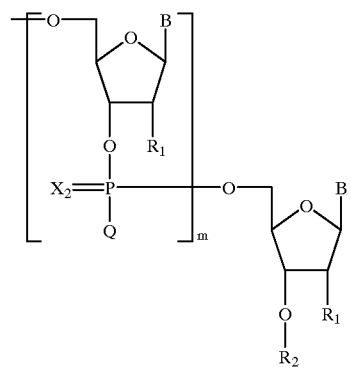

wherein:

each $R_1$, is, independently, H, —OH, —F, —O—$X_3$—D;

$X_3$ is alkyl having from 1 to 10 carbons;

D is H, amino, protected amino, alkyl substituted amino, imidazole, or (—O—$X_3$)$_p$, where p is 1 to about 10;

each $X_2$ is O or S;

$R_5$ is —N($R_6$)$_2$, or a heterocycloalkyl or heterocycloalkenyl ring containing from 4 to 7 atoms, and having up to 3 heteroatoms selected from nitrogen, sulfur, and oxygen;

each Q is —$X_1$H or

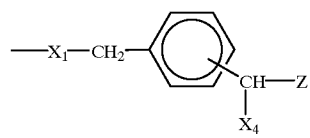

m is 0 to about 50;

each B, independently, is a naturally occurring or non-naturally occurring nucleobase or a protected naturally occurring or non-naturally occurring nucleobase; and $R_7$ is $R_5$, or has the Formula IX:

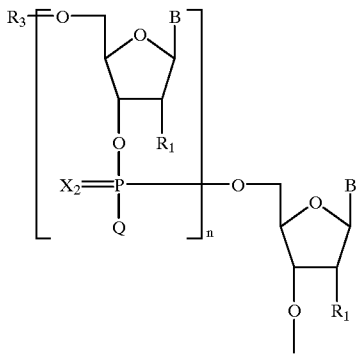

wherein:
$R_3$ is hydrogen, a hydroxyl protecting group, or a linker connected to a solid support; and
n is 0 to about 50; with the proviso that the sum of m and n do not exceed 50;
$X_4$ is Z or H;

Z is CN, $-Si(R_9)_3$, halogen, $NO_2$, alkaryl, sulfoxyl, sulfonyl, thio, substituted sulfoxyl, substituted sulfonyl, or substituted thio, wherein said substituent is alkyl, aryl, or alkaryl;

each $R_9$ is, independently, alkyl having 1 to about 10 carbon atoms, or aryl having 6 to about 10 carbon atoms.

In some preferred embodiments of the compounds of the invention, Z is CN. In further preferred embodiments, $X_4$ is H, and Z is CN. In other preferred embodiments $X_4$ is H, and Z is $Si(R_9)_3$. In further preferred embodiments A is H or $-P(R_5)_2$.

In some preferred embodiments $R_5$ is $-N(CH(CH_3)_2)_2$, and in other preferred embodiments $R_7$ has Formula IX.

Preferably, n is 1 to 30, with 1 to about 20 being more preferred. In some preferred embodiments n is 0.

In more preferred embodiments, $X_4$ is H, Z is CN, $X_1$ is O, and A is H; or $X_4$ is H, Z is CN, $X_1$ is S, and A is H. In other preferred embodiments $X_4$ is H, Z is CN, $X_1$ is O, and each $R_6$ is isopropyl. In further preferred embodiments $X_4$ is H, Z is CN, $X_1$ is S, and each $R_6$ is isopropyl.

In some particularly preferred embodiments, the compounds of the invention have Formula X:

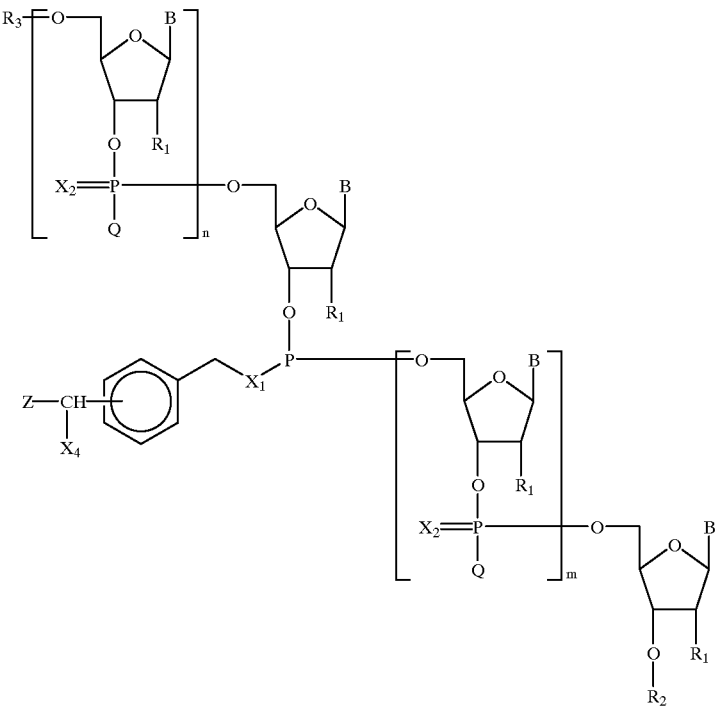

or the Formula XI:

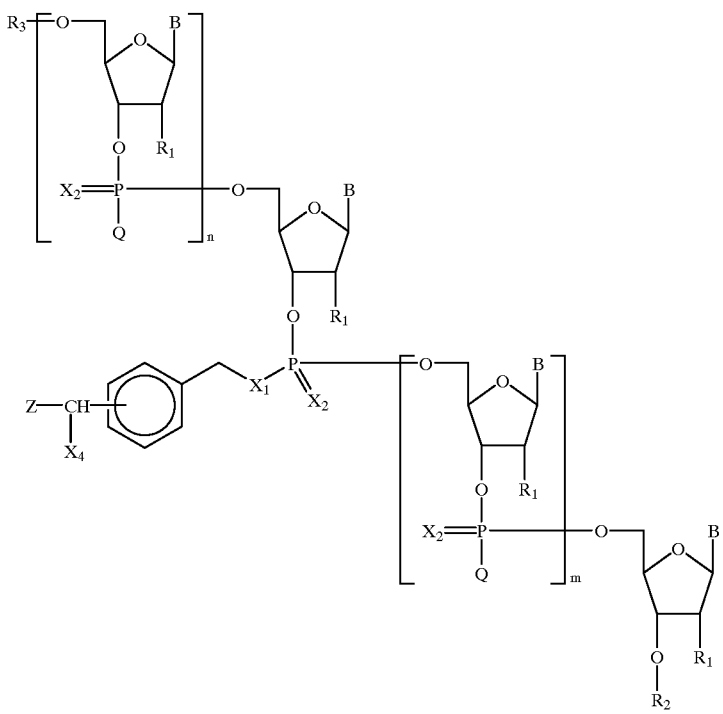

wherein $R_2$ is H, or preferably, a linker connected to a solid support, and —CH($X_4$)—Z is preferably in the ortho or para position.

In preferred embodiments m and n are each 0; or $X_4$ is H, Z is CN, and $X_1$ is O.

Also provided in accordance with the present invention are compounds having the formula:

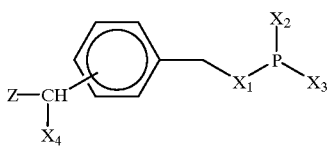

wherein Z, $X_4$ and $X_1$ are as defined above, $X_2$ is halogen, and $X_3$ is —N($R_6$)$_2$, or a heterocycloalkyl or heterocycloalkenyl ring containing from 4 to 7 atoms, and having up to 3 heteroatoms selected from nitrogen, sulfur, and oxygen. In some preferred embodiments, Z is CN. In further preferred embodiments, $X_1$ is O. In still further preferred embodiments, $X_3$ is —N($R_6$)$_2$ where $R_6$ is isopropyl. Preferably, $X_2$ is chlorine.

The present invention also provides products produced by the methods of the invention.

DESCRIPTION OF PREFERRED EMBODIMENTS

The present invention provides methods for the preparation of oligomeric compounds having phosphite, phosphodiester, phosphorothioate, or phosphorodithioate linkages, and also of intermediates useful in their preparation.

In some preferred embodiments of the invention, methods are provided for the preparation of an oligomeric compound comprising at least one moiety having the Formula I:

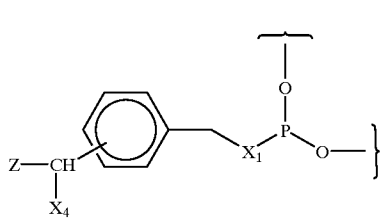

wherein:

$X_4$ is Z or H;

Z is CN, halogen, $NO_2$, alkaryl, sulfoxyl, sulfonyl, thio, substituted sulfoxyl, substituted sulfonyl, or substituted thio, wherein said substituent is alkyl, aryl, or alkaryl;

$X_1$ is O or S;

comprising the steps of:

(a) providing a compound having the Formula II:

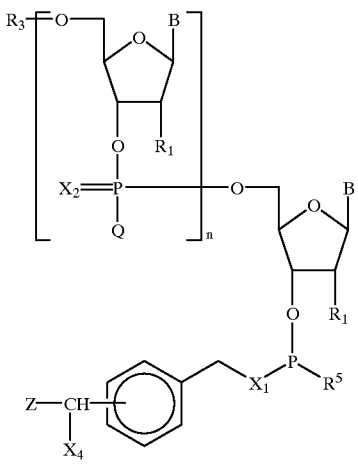

wherein:

each $R_1$, is, independently, H, —OH, —F, or —O—$X_3$—D;

$X_3$ is alkyl having from 1 to 10 carbons;

D is H, amino, protected amino, alkyl substituted amino, imidazole, or (—O—$X_3$)$_p$, where p is 1 to about 10;

each $X_2$ is O or S;

$R_3$ and $R_{3a}$ are each hydrogen, a hydroxyl protecting group, or a linker connected to a solid support;

each B, independently, is a naturally occurring or non-naturally occurring nucleobase or a protected naturally occurring or non-naturally occurring nucleobase;

n is 0 to about 50;

each Q is —$X_1$H or

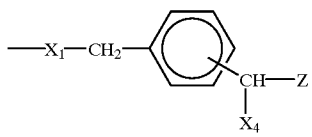

$R_5$ is —N($R_6$)$_2$, or a heterocycloalkyl or heterocycloalkenyl ring containing from 4 to 7 atoms, and having up to 3 heteroatoms selected from nitrogen, sulfur, and oxygen; and $R_6$ is straight or branched chain alkyl having from 1 to 10 carbons; and (b) reacting the compound of Formula II with a compound having Formula III:

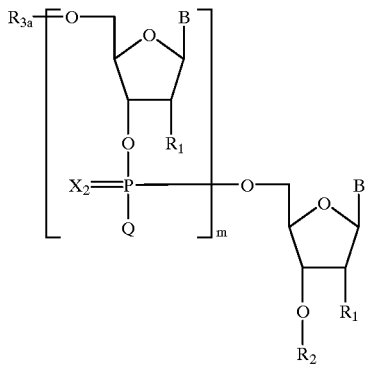

wherein $R_{3a}$ is hydrogen; and $R_2$ is a hydroxyl protecting group, or a linker connected to a solid support, provided that $R_2$ and $R_{3a}$ are not both simultaneously a linker connected to a solid support; to form the oligomeric compound.

The methods of the present invention are useful for the preparation of oligomeric compounds containing monomeric subunits that are joined by a variety of linkages, including phosphite, phosphodiester, phosphorothioate, and/or phosphorodithioate linkages.

As used herein, the term "oligomeric compound" is used to refer to compounds containing a plurality of monomer subunits that are joined by phosphorus-containing linkages, such as phosphite, phosphodiester, phosphorothioate, and/or phosphorodithioate linkages. Oligomeric compounds therefore include oligonucleotides, their analogs, and synthetic oligonucleotides. Monomer or higher order synthons having Formulas II or III above include both native (i.e., naturally occurring) and synthetic (e.g., modified native or totally synthetic) nucleosides.

In preferred embodiments, protected phosphoramidites are reacted with a free hydroxyl group of a compound of Formula III to produce phosphite compounds containing the linkage of Formula I. Preferably, capping and/or oxidation or sulfurization steps are performed to produce a compound of Formula IV.

Methods for coupling compounds of Formula II and Formula III of the invention include both solution phase and solid phase chemistries. Representative solution phase techniques are described in U.S. Pat. No. 5,210,264, which is assigned to the assignee of the present invention. In preferred embodiments, the methods of the present invention are employed for use in iterative solid phase oligonucleotide synthetic regimes. Representative solid phase techniques are those typically employed for DNA and RNA synthesis utilizing standard phosphoramidite chemistry, (see, e.g., Protocols For Oligonucleotides And Analogs, Agrawal, S., ed., Humana Press, Totowa, N.J., 1993, hereby incorporatedby reference in its entirety). A preferred synthetic solid phase synthesis utilizes phosphoramidites as activated phosphate compounds. In this technique, a phosphoramidite monomer is reacted with a free hydroxyl on the growing oligomer chain to produce an intermediate phosphite compound, which is subsequently oxidized to the $p^v$ state using standard methods. This technique is commonly used for the synthesis of several types of linkages including phosphodiester, phosphorothioate, and phosphorodithioate linkages.

Typically, the first step in such a process is attachment of a first monomer or higher order subunit containing a protected 5'-hydroxyl to a solid support, usually through a linker, using standard methods and procedures known in the art. The support-bound monomer or higher order first synthon is then treated to remove the 5'-protecting group, to form a compound of Formula III wherein $R_2$ is a linker connected to a solid support. Typically, this is accomplished by treatment with acid. The solid support bound monomer is then reacted with a compound of Formula II to form a compound of Formula IV, which has a phosphite or thiophosphite linkage of Formula I. In preferred embodiments, synthons of Formula II and Formula III are reacted under anhydrous conditions in the presence of an activating agent such as, for example, 1H-tetrazole, 5-(4-nitrophenyl)-1H-tetrazole, or diisopropylamino tetrazolide.

In preferred embodiments, phosphite or thiophosphite compounds containing a linkage of Formula I are oxidized or sulfurized as shown below to produce compounds having a linkage of Formula XII, where $X_1$ and $X_2$ can each be O or S:

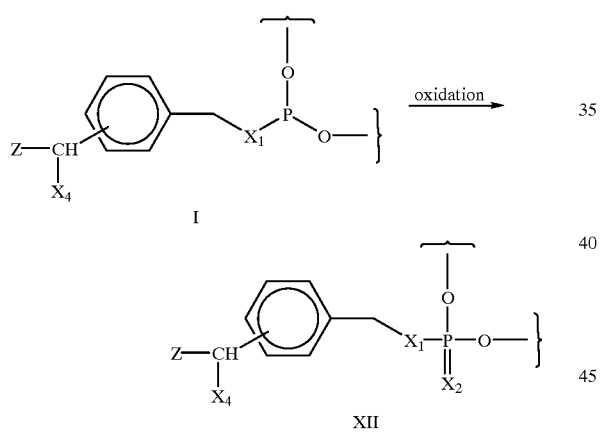

Choice of oxidizing or sulfurizing agent will determine whether the linkage of Formula I will be oxidized or sulfurized to a phosphotriester, thiophosphotriester, or a dithiophosphotriester linkage.

It is generally preferable to perform a capping step, either prior to or after oxidation or sulfurization of the phosphite triester, thiophosphite triester, or dithiophosphite triester. Such a capping step is generally known to be beneficial by preventing shortened oligomer chains, by blocking chains that have not reacted in the coupling cycle. One representative reagent used for capping is acetic anhydride. Other suitable capping reagents and methodologies can be found in U.S. Pat. No. 4,816,571, issued Mar. 28, 1989, hereby incorporated by reference in its entirety.

Treatment with an acid removes the 5'-hydroxyl protecting group, and thus transforms the solid support bound oligomer into a further compound of Formula III wherein $R_{3a}$ is hydrogen, which can then participate in the next synthetic iteration; i.e., which can then be reacted with a further compound of Formula II. This process is repeated until an oligomer of desired length is produced.

The completed oligomer is then cleaved from the solid support. The cleavage step, which can precede or follow deprotection of protected functional groups, will yield a compound having Formula IV wherein $R_2$ is hydrogen. During cleavage, the linkages between monomeric subunits are converted from phosphotriester, thiophosphotriester, or dithiophosphotriester linkages to phosphodiester, phosphorothioate, or phosphorodithioate linkages. This conversion is effected through the loss of an oxygen or sulfur protecting group of Formula XIII, XIV or XV:

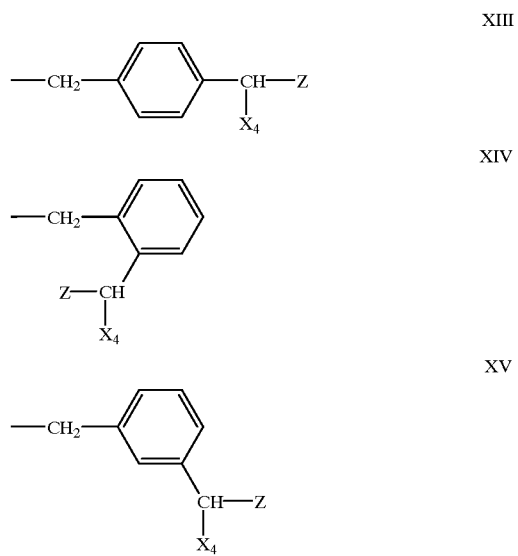

Depending upon the species Z, it is believed that the loss of the oxygen or sulfur protecting group or Formula XIII or XIV occurs respectively via either a ζ-elimination mechanism, or a δ-elimination mechanism.

In some preferred embodiments, where the moiety —CH($X_4$)—Z is electron withdrawing, the moiety —CH($X_4$)—Z is preferably in the ortho or para position of the phenyl ring; that is, it is attached to the ring carbon that is either next to or opposite from the carbon to which the remainer of the molecule is attached.

In other preferred embodiments where the moiety —CH($X_4$)—Z is electron releasing, the moiety —CH($X_4$)—Z is preferably in the meta postition of the phenyl ring.

While not wishing to be bound by a particular theory, it is believed that the loss of the oxygen or sulfur protecting group of formula XIII where Z is a non-silyl electron withdrawing group occurs via a ζ-elimination mechanism, illustrated in Scheme I below:

Scheme I

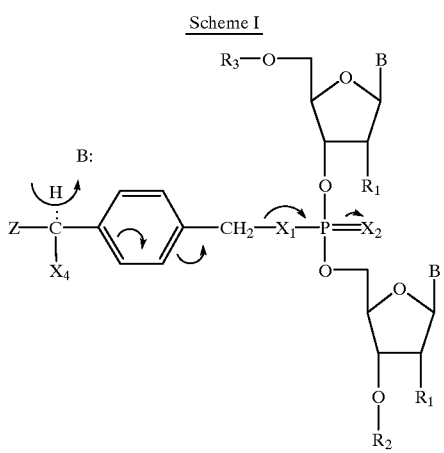

In this mechanism, a base first abstracts an acidic proton from the carbon atom adjacent to electron withdrawing group Z. The resonant movement of electrons as depicted in Scheme I above is believed to cause the loss of the oxygen or sulfur protecting group via a ζ-elimination, thereby forming a phosphodiester, phosphorothioate, or phosphorodithioate linkage. The other product of the deprotection is a conjugated triene, having electron withdrawing substituent Z at the terminal position.

Similarly, it is believed that the loss of the oxygen or sulfur protecting group of formula XIV where Z is a non-silyl electron withdrawing group occurs via a δ-elimination mechanism, illustrated in Scheme II below:

Scheme II

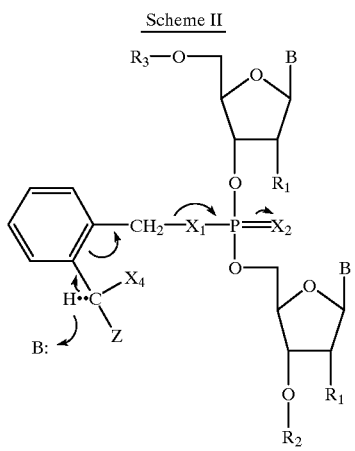

After base abstraction of an acidic proton from the carbon atom adjacent to electron withdrawing group Z, the resonant movement of electrons as depicted in Scheme II above is believed to cause the loss of the oxygen or sulfur protecting group via a δ-elimination, thereby forming a phosphodiester, phosphorothioate, or phosphorodithioate linkage. The other product of the deprotection is a cojugated cyclic compound, having electron withdrawing substituent Z at the terminal position.

In some prefereed embodiments of the compounds of the invention, substituent Z can be an electron withdrawing group selected such that it facilitates the abstraction of a proton from the adjacent carbon atom by resonance, inductive, or other electron withdrawing mechanisms. Accordingly, Z can be any of a variety of electron withdrawing substituents, provided that it does not otherwise interfere with the methods of the invention. Preferred non-silyl electron withdrawing Z groups include CN, halogens, $NO_2$, alkaryl groups, sulfoxyl groups, sulfonyl groups, thio groups, substituted sulfoxyl groups, substituted sulfonyl groups, or substituted thio groups, wherein the substituents are selected from the group consisting of alkyl, aryl, or alkaryl. In more preferred embodiments Z is cyano.

Z can also be a trisubstituted silyl moiety, wherein the substituents are alkyl, aryl or both. While not wishing to be bound by a particular theory, it is believed that the loss of the oxygen or sulfur protecting group of formula XIII where Z is a trisubstituted silyl moiety, occurs via a ζ-fragmentation mechanism, illustrated in Scheme III below:

Scheme III

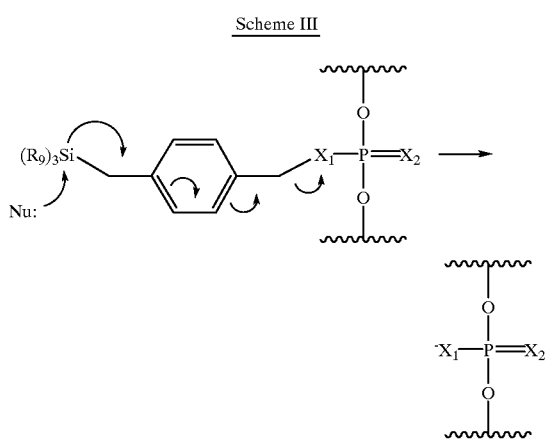

In this mechanism, a nucleophile attacks the silyl silicon atom, and the resonant movement of electrons as depicted in Scheme II above is believed to cause the loss of the oxygen or sulfur protecting group via a ζ-fragmentation mechanism, thereby forming a phosphodiester, phosphorothioate, or phosphorodithioate linkage. The other products of the deprotection are believed to be a conjugated cyclic system and $Nu-Si(R_3)_3$.

Similarly, it is believed that the loss of the oxygen or sulfur protecting group of formula XIV where Z is a trisubstituted silyl moiety occurs via a δ-fragmemtation mechanism, illustrated in Scheme IV below:

Scheme IV

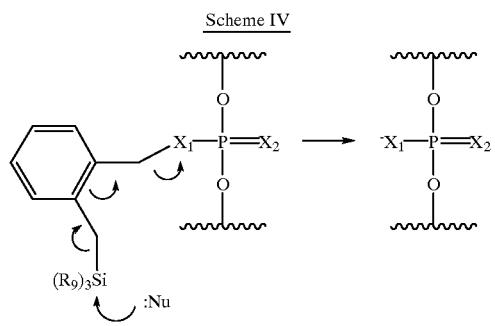

After attack upon silicon by a nucleophile, the resonant movement of electrons as depicted in Scheme IV above is believed to cause the loss of the oxygen or sulfur protecting group via a δ-fragmentation mechanism, thereby forming a phosphodiester, phosphorothioate, or phosphorodithioate linkage. The other products of the deprotection are believed to be a conjugated cyclic system and $Nu-Si(R_3)_3$.

A wide variety of bases can be used to initiate the δ-elimination or ζ-elimination of the oxygen or sulfur protecting groups of formula XIII or XIV. These include aqueous ammonium hydroxide, aqueous methylamine, or DBU (1,8-diazabicyclo[5.4.0]undec-7-ene).

A wide variety of nucleophiles can be used to initiate the δ-fragmentation or ζ-fragmentation of the oxygen or sulfur protecting groups of formulas XIII or XIV. These include ammonium hydroxide, fluoride ion, alkyl amines, aqueous bases, and alkyl amines in combination with ammonium hydroxide. The resulting products include phosphate, phosphorothioate, and phosphorodithioate containing compounds.

Contact with fluoride ion preferably is effected in a solvent such as tetrahydrofuran, acetonitrile, dimethoxyethane, or water. Fluoride ion preferably is provided in the form of one or more salts selected from tetraalkylammonium fluorides (e.g., tetrabutylammonium fluoride (TBAF)), potassium fluoride, or cesium fluoride.

Preferably, conditions for removal of the oxygen or sulfur protecting group via elimination or fragmentation mechanisms described above also effect cleavage of the oligomeric compound from the solid support.

The methods of the present invention are applicable to the synthesis of a wide variety of oligomeric compounds which contain phosphite, phosphodiester, phosphorothioate, or phosphorodithioate linkages. As used herein, the term "oligomeric compound" denotes a polymeric compound containing two or more monomeric subunits joined by such phosphite, phosphodiester, phosphorothioate, or phosphorodithioate linkages.

In preferred embodiments, the methods of the invention are used for the preparation of oligonucleotides and their analogs. As used herein, the term "oligonuclotide analog" means compounds that can contain both naturally occurring (i.e. "natural") and non-naturally occurring ("synthetic") moieties, for example, nucleosidic subunits containing modified sugar and/or nucleobase portions. Such oligonucleotide analogs are typically structurally distinguishable from, yet functionally interchangeable with, naturally occurring or synthetic wild type oligonucleotides. Thus, oligonucleotide analogs include all such structures which function effectively to mimic the structure and/or function of a desired RNA or DNA strand, for example, by hybridizing to a target. The term synthetic nucleoside, for the purpose of the present invention, refers to a modified nucleoside. Representative modifications include modification of a heterocyclic base portion of a nucleoside to give a non-naturally occurring nucleobase, a sugar portion of a nucleoside, or both simultaneously.

Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, P. D., *Anti-Cancer Drug Design*, 1991, 6, 585–607, each of which are hereby incorporated by reference in their entirety. The term 'nucleosidic base' is further intended to include heterocyclic compounds that can serve as like nucleosidic bases including certain 'universal bases' that are not nucleosidic bases in the most classical sense but serve as nucleosidic bases. Especially mentioned as a universal base is 3-nitropyrrole.

Representative 2' sugar modifications (position $R_1$) amenable to the present invention include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and (PEG)-containing groups, such as crown ethers and those which are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249, each of which are hereby incorporated by reference in their entirety. Further sugar modifications are disclosed in Cook, P. D., supra. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled Oligomeric Compounds having Pyrimidine Nucleotide(s) with 2' and 5' Substitutions, hereby incorporated by reference in its entirety.

Sugars having O-substitutions on the ribosyl ring are also amenable to the present invention. Representative substitutions for ring O include S, $CH_2$, CHF, and $CF_2$, see, e.g., Secrist, et al., *Abstract 21, Program & Abstracts, Tenth International Roundtable, Nucleosides, Nucleotides and their Biological Applications*, Park City, Utah, Sep. 16–20, 1992, hereby incorporated by reference in its entirety.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety.

As used herein, the term "aralkyl" denotes alkyl groups which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

As used herein, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

In some preferred embodiments of the invention $R_2$, $R_3$ or $R_{3a}$ can be a linker connected to a solid support. Solid supports are substrates which are capable of serving as the solid phase in solid phase synthetic methodologies, such as those described in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069. Linkers are known in the art as short molecules which serve to connect a solid support to functional groups (e.g., hydroxyl groups) of initial synthon molecules in solid phase synthetic techniques. Suitable linkers are disclosed in, for example,

*Oligonucleotides And Analogues A Practical Approach*, Ekstein, F. Ed., IRL Press, N.Y, 1991, Chapter 1, pages 1–23, hereby incorporated by reference in its entirety.

Solid supports according to the invention include those generally known in the art to be suitable for use in solid phase methodologies, including, for example, controlled pore glass (CPG), oxalyl-controlled pore glass (see, e.g., Alul, et al., *Nucleic Acids Research* 1991, 19, 1527, hereby incorporated by reference in its entirety), TentaGel Support—an aminopolyethyleneglycol derivatized support (see, e.g., Wright, et al., *Tetrahedron Letters* 1993, 34, 3373, hereby incorporated by reference in its entirety) and Poros—a copolymer of polystyrene/divinylbenzene.

In some preferred embodiments of the invention $R_2$, $R_3$ or $R_{3a}$ can be a hydroxyl protecting group. A wide variety of hydroxyl protecting groups can be employed in the methods of the invention. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage, et al., *Tetrahedron* 1992, 48, 2223–2311, and also in Greene and Wuts, *Protective Groups in Organic Synthesis*, Chapter 2, 2d ed, John Wiley & Sons, New York, 1991, each of which are hereby incorporated by reference in their entirety. Preferred protecting groups used for $R_2$, $R_3$ and $R_{3a}$ include dimethoxytrityl (DMT), monomethoxytrityl, 9-phenylxanthen-9-yl (Pixyl) and 9-(p-methoxyphenyl)xanthen-9-yl (Mox). The $R_2$ or $R_3$ group can be removed from oligomeric compounds of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See for example, Greene and Wuts, supra.

In some preferred embodiments of the invention amino groups are appended to alkyl or other groups, such as, for example, 2'-alkoxy groups (e.g., where $R_1$ is alkoxy). Such amino groups are also commonly present in naturally occurring and non-naturally occurring nucleobases. It is generally preferred that these amino groups be in protected form during the synthesis of oligomeric compounds of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected" when used in connection with a molecular moiety such as "nucleobase" indicates that the molecular moiety contains one or more functionalities protected by protecting groups.

Sulfurizing agents used during oxidation to form phosphorothioate and phosphorodithioate linkages include Beaucage reagent (see e.g. Iyer, R. P., et.al., *J. Chem. Soc.*, 1990, 112, 1253–1254, and Iyer, R. P., et.al., *J. Org. Chem.*, 1990, 55, 4693–4699); tetraethylthiuram disulfide (see e.g., Vu, H., Hirschbein, B. L., *Tetrahedron Lett.*, 1991, 32, 3005–3008); dibenzoyl tetrasulfide (see e.g., Rao, M. V., et.al., *Tetrahedron Lett.*, 1992, 33, 4839–4842); di(phenylacetyl)disulfide (see e.g., Kamer, P. C. J., *Tetrahedron Lett.*, 1989, 30, 6757–6760); Bis(O,O-diisopropoxy phosphinothioyl)disulfids (see Stec et al., *Tetrahedron Lett.*, 1993, 34, 5317–5320); 3-ethoxy-1,2,4-dithiazoline-5-one (see *Nucleic Acids Research*, 1996 24, 1602–1607, and *Nucleic Acids Research*, 1996 24, 3643–3644); Bis(p-chlorobenzenesulfonyl)disulfide (see *Nucleic Acids Research*, 1995 23, 4029–4033); sulfur, sulfur in combination with ligands like triaryl, trialkyl, triaralkyl, or trialkaryl phosphines. The foregoing references are hereby incorporated by reference in their entirety.

Useful oxidizing agents used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization the reaction is performed under anhydrous conditions with the exclusion of air, in particular oxygen whereas in the case of oxidation the reaction can be performed under aqueous conditions.

Oligonucleotides or oligonucleotide analogs according to the present invention hybridizable to a specific target preferably comprise from about 5 to about 50 monomer subunits. It is more preferred that such compounds comprise from about 10 to about 30 monomer subunits, with 15 to 25 monomer subunits being particularly preferrred. When used as "building blocks" in assembling larger oligomeric compounds (i.e., as synthons of Formula II), smaller oligomeric compounds are preferred. Libraries of dimeric, trimeric, or higher order compounds of general Formula II can be prepared for use as synthons in the methods of the invention. The use of small sequences synthesized via solution phase chemistries in automated synthesis of larger oligonucleotides enhances the coupling efficiency and the purity of the final oligonucloetides. See for example: Miura, K., et al., *Chem. Pharm. Bull.*, 1987, 35, 833–836; Kumar, G., and Poonian, M. S., *J. Org. Chem.*, 1984, 49, 4905–4912; Bannwarth, W., *Helvetica Chimica Acta*, 1985, 68, 1907–1913; Wolter, A., et al., *Nucleotides and Nucleosides*, 1986, 5, 65–77, each of which are hereby incorporated by reference in their entirety.

In one aspect of the invention, the compounds of the invention are used to modulate RNA or DNA, which code for a protein whose formation or activity it is desired to modulate. The targeting portion of the composition to be employed is, thus, selected to be complementary to the preselected portion of DNA or RNA, that is to be hybridizable to that portion.

In some preferred embodiments of the methods of the invention, compounds of Formula II are prepared by reaction of a protected nucleoside having Formula V:

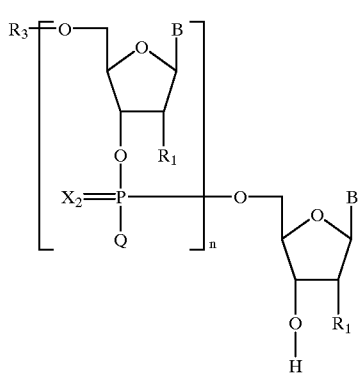

and a phosphine compound of Formula VI:

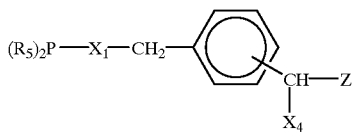

VI in the presence of an acid. Suitable acids include those known in the art to be useful for coupling of phosphoramidites, including, for example, diisopropylammonium tetrazolide.

Compounds of Formula VI are preferably prepared by reacting an alcohol having the formula $HOCH_2C_6H_4(-CH(X_4)-Z)$ with phosphorus trichloride, and reacting the resultant product, $Cl_2PX_1CH_2C_6H_3(-CH(X_4)-Z)$, with at least two equivalents of an amine having the formula $[(R_6)_2N]_2NH$. Each of the $R_6$ groups can be the same or different, and are preferably alkyl having 1 to about 10 carbon atoms, more preferably 1 to 6 carbon atoms, with 3 carbon atoms, and particularly isopropyl groups, being especially preferred.

Additionally, compounds of Formula II can be prepared by reaction of protected nucleosides with a chlorophosphine compound of formula $ClP[i-Pr_2N]_2$, followed by reaction with a compound of Formula XX:

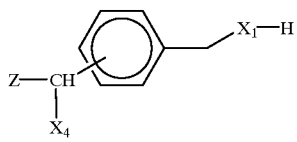

XX in the presence of an acid.

Therefore, also provided in accordance with the present invention are methods for the preparation of a protected nucleoside phosphoramidite of formula II:

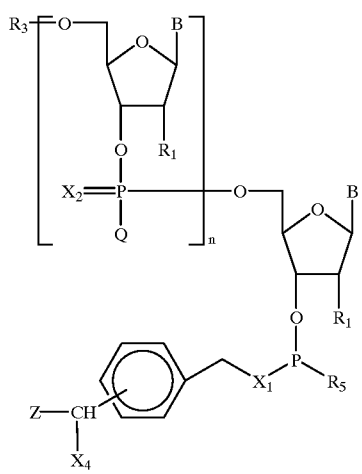

II wherein:

$X_4$, Z, $X_1$, $R_1$, $X_2$, $R_3$, B, n, Q and $R_5$ are defined as above;

comprising:

selecting a protected nucleoside of formula V:

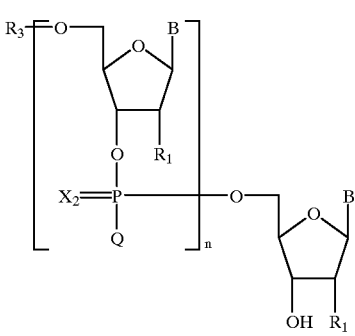

V reacting the protected nucleoside with a chlorophosphine compound of formula $ClP(R_5)_2$ in the presence of a base; and protecting the product by reaction with a compound of formula XX:

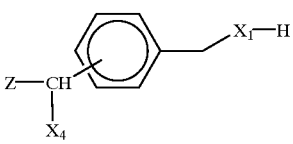

XX in the presence of an acid;

to form the protected nucleoside phosphoramidite.

In particularly preferred embodiments of the foregoing methods, Z is CN, $X_4$ is H, and the moiety $—CH(X_4)—Z$ is in the ortho or para position, with the para position being preferred, $R_5$ is diisopropylamino, and n is 0.

Scheme 5 below describes the preparation of mononucleotide phosphoramidites of the invention, i.e., compounds of Formula IV where n is 0:

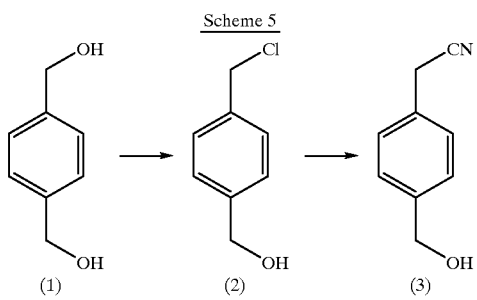

Scheme 5

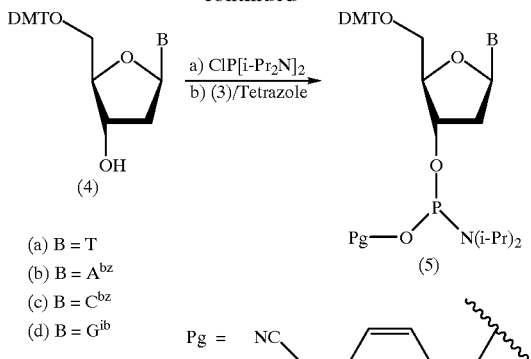

(a) B = T
(b) B = A$^{bz}$
(c) B = C$^{bz}$
(d) B = G$^{ib}$

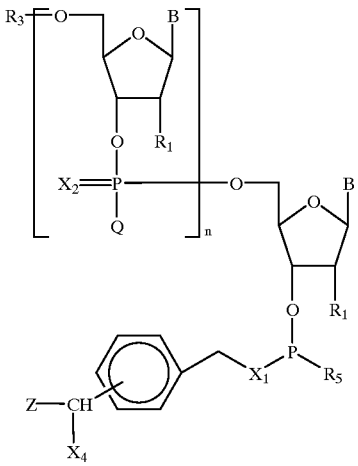

In the compounds and methods of the present inventon, $X_1$ and $X_2$ can each independently be O or S. Thus, compounds having chiral phosphorus linkages are contemplated by the present invention. See Stec, W. J., and Lesnikowski, Z. J., in *Methods in Molecular Biology* Vol. 20: *Protocols for oligonucleotides and Analogs*, S. Agrawal, Ed., Humana Press, Totowa, N.J. (1993), at Chapter 14. See also Stec, W. J. et al., *Nucleic Acids Research*, Vol. 19, No. 21, 5883–5888 (1991); and European Patent Application EP 0 506 242 A1, each of which are hereby incorporated by reference in their entirety.

Also provided in preferred embodiments of the invention are compounds having the general Formula VII:

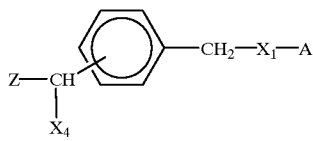

VII wherein $X_1$, A, $X_4$ and Z are as defined above.

Particularly preferred embodiments of the compounds of the invention have the formula II:

wherein:

$X_4$, Z, $X_1$, $R_1$, $X_2$, $R_3$, B, n, Q and $R_5$ are defined as above. In some especially preferred embodiments of the compounds of the invention having formula II above, Z is CN, $X_4$ is H the moiety —$CH_2$—Z is in the ortho or para position, with the para position being preferred, $R_5$ is diisopropylamino, and n is 0.

The oligomeric compounds of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLE 1

4-Chloromethylbenzyl Alcohol

Benzenedimethanol was monochlorinated to produce the title compound (2) according to the procedure of Pierce, M., et al., *J. Org. Chem.* 1996, 61, 444–450, which is incorporated herein in its entirety.

EXAMPLE 2

Preparation of Cyano Alcohol

The chloro alcohol (2) (214 mmol) and sodium iodide (2.14 mmol) were taken up in anhydrous acetonitrile (500 ml) in a 1 L round bottomed flask. Potassium cyanide (321 mmol; 1.5 eqiv.) was added all at once and the mixture stirred at room temperature until the reaction was complete, as determined by $^{13}C$ NMR. The reaction mixture was filtered and the solid washed with ethyl acetate (200 ml). Concentration of the filtrate followed by distillation using a short path gave the cyano alcohol (3) as a colorless solid.

Alternatively, (3) can be prepared using sodium cyanide in DMF instead of KCN in acetonitrile in the procedure described above.

EXAMPLE 3

General Method I for the Synthesis of Phosphoramidites

A 500 mL two-necked flask equipped with a magnetic stirrer, a gas inlet for argon, and a septum was assembled under an argon atmosphere. All glassware was dried at 120° C. for 1 hour. The flask was then charged with bis(diisopropylamino) chlorophosphine (84.6 mmol), Hünigs base (diisopropylethylamine) (105.8 mmol) and anhydrous dichloromethane (250 ml). DMT-protected deoxyribonucleoside (4a–d) (70.5 mmol) was added as a solid over a period of 10 minutes, with stirring. After 30 minutes, all the volatiles were removed under vacuum (oil pump) and the residue dissolved in anhydrous acetonitrile (150 ml). A solution of the cyano alcohol (3) (105.7 mmol) in acetonitrile (100 ml) was added followed by 1H-tetrazole (63 mmol). Stirring was continued for a further 1 hour. The reaction mixture was then concentrated, and the residue was redissolved in dichloromethane (500 ml), washed with sodium bicarbonate solution and dried ($Na_2SO_4$). Concentration of the dried solution afforded the crude material which was purified by silica gel flash chromatography. The fractions corresponding to the amidites were combined and concentrated to give the pure product as a foamy solid, with yields of 65–80% depending on the nucleoside.

EXAMPLE 4

Preparation of 4-Cyanomethylbenzyl N,N,N',N'-Tetraisopropylphosphoramidite

A 500 mL three-necked flask equipped with a magnetic stirrer, a glass stopper and an inlet for argon is assembled under argon atmosphere. All glassware is dried in an oven at 120° C. for 1 hour. The reaction flask is charged with anhydrous ether (150 mL) and phosphorous trichloride (9.27 g; 67.5 mmol). 4-Cyanomethylbenzyl alcohol (50 mmol) in ether (100 mL) is added to the reaction flask slowly with stirring at 0° C. (ice cooling) using a pressure-equalized addition funnel. After addition is complete, the ice bath is removed and the reaction is stirred for three hours. The reaction mixture then is transferred to a 500 mL flask and concentrated under reduced pressure. To this product in anhydrous ether (200 mL) is added diisopropylamine (57.7 mL) at 0° C. under argon. After the addition is complete, stirring is continued at room temperature for 16 hours (or overnight). The reaction mixture is filtered and concentrated to afford the product.

EXAMPLE 5

General Method II for the Preparation of Phosphoramidites

A 250 mL two-necked flask equipped with a magnetic stirrer, a gas inlet for argon, and a septum is assembled under an argon atmosphere. All glassware are dried at 120° C. for 1 hour. The flask is charged with 5'-O-DMT nucleoside (7 mmol) and 1H-tetrazole (5.6 mmol). Anhydrous acetonitrile (50 mL) is then added. To this stirred mixture under argon at room temperature is added a solution of 4-cyanomethylbenzyl N,N,N',N'-tetraisopropylphosphoramidite (10.5 mmol) in acetonitrile (50 mL). Standard workup followed by purification afforded the phosphoramidites.

EXAMPLE 6

Synthesis of T-T Phosphorothioate Dimer 100 milligram (4 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with dichloromethane and then with acetonitrile. A 0.2 M solution of 5'-O-(4,4'-dimethoxytrityl)thymidine-3'-O-(4-cyanomethylbenzyl)-N,N-diisopropylphosphoramidite in acetonitrile and a 0.4 M solution of 1H-tetrazole in acetonitrile is then added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes. The aqueous solution is filtered and concentrated under reduced pressure to give the phosphorothioate T-T dimer.

EXAMPLE 7

Synthesis of C-T Phosphorothioate Dimer 100 milligram (4 mmole) of 5'-O-Dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2 M solution of $N^4$-Benzoyl-5'-O-(4,4'-dimethoxytrityl)-2'-deoxycytidine-3'-O-(4-cyanomethylbenzyl)-N,N-diisopropylphosphoramidite) in acetonitrile and a 0.4 M solution of 1H-tetrazole in acetonitrile are added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes and then incubated at 55° C. for 12 hours. The aqueous solution is filtered, concentrated under reduced pressure and then treated at room temperature with 1.0 M solution of tetra-n-butyl ammonium fluoride in THF to give a phosphorothioate dimer of dC-T.

EXAMPLE 8

Synthesis of 5'-TTTTTTT-3' Phosphorothioate Heptamer 50 milligram (2 mmole) of 5'-O-Dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile. Then, a 0.2 M solution of 5'-O-(4,4'-dimethoxytrityl)thymidine-3'-O-(4-cyanomethylbenzyl)-N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

This complete cycle is repeated five more times to get the completely protected thymidine heptamer. The carrier containing the compound is treated with 30% aqueous ammonium hydroxide solution for 90 minutes at room temperature. The aqueous solution is filtered, concentrated under reduced pressure to give a phosphorothioate heptamer of TTTTTTT.

EXAMPLE 9

Synthesis of 5'-d(GACTT)-3' Phosphorothioate Tetramer 50 milligram (2 mmole) of 5'-O-dimethoxytritylthymidine bonded to CPG (controlled pore glass) through an ester linkage is taken in a glass reactor, and a dichloromethane solution of 2% dichloroacetic acid (volume/volume) is added to deprotect the 5'-hydroxyl group. The product is washed with acetonitrile, and a 0.2 M solution of 5'-O-(4,4'-dimethoxytrityl)thymidine-3'-O-(4-cyanomethylbenzyl)-N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile, and a 0.2 M solution of $N^4$-benzoyl-5-O-(4,4'-dimethoxytrityl)-2'-deoxycytidine-3'-O-(4-cyanomethylbenzyl)-N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2 M solution of $N^6$-benzoyl-5'-O-(4,4'-dimethoxytrityl)-2'-deoxyadenosine-3'-O-(4-cyanomethylbenzyl)-N,N-diisopropylphosphoramidite) in anhydrous acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

A dichloromethane solution of 2% dichloroacetic acid (volume/volume) is added to deprotect the 5'-hydroxyl group. The product is washed with acetonitrile. Then, a 0.2 M solution of $N^2$-isobutyryl-5'-O-(4,4'-dimethoxytrityl)-2'-deoxyguanosine-3'-O-(4-cyanomethylbenzyl)-N,N-diisopropylphosphoramidite) in acetonitrile and a 0.4 M solution of 1H-tetrazole in acetonitrile is added, and reacted at room temperature for 5 minutes. The product is washed with acetonitrile, and then a 0.05 M solution of Beaucage reagent in acetonitrile is added and reacted at room temperature for 5 minutes. This sulfurization step is repeated one more time for 5 minutes. The support is washed with acetonitrile and then a solution of acetic anhydride/lutidine/THF (1:1:8), and N-methyl imidazole/THF is added to cap the unreacted 5'-hydroxyl group. The product is washed with acetonitrile.

The carrier containing the compound is treated with 30% aqueous ammonium hydroxide solution for 90 minutes at room temperature and then incubated at 55° C. for 16 hour. The aqueous solution is filtered, concentrated under reduced pressure to give a phosphorothioate tetramer of 5'-d (GACTT)-3'.

EXAMPLE 10

Synthesis of Fully-Modified 5'-d(TCC-CGC-CTG-TGA-CAT-GCA-TT)-3' Phosphorothioate 20-mer The synthesis of the above sequence was performed on a Pharmacia OligoPilot II Synthesizer on a 620 μmole scale using the cyanomethylbenzyl phosphoramidites and Pharmacia's primar support. Detritylation was performed using 3% dichloroacetic acid in dichloromethane (volume/volume). Sulfurization was performed using a 0.2 M solution of Beaucage reagent in acetonitrile for 2 minutes. At the end of synthesis, the support was washed with acetonitrile, cleaved, deprotected and purified as described above.

EXAMPLE 11

Synthesis of Fully-Modified 5'-d(GCC-CAA-GCT-GGC-ATC-CGT-CA)-3' Phosphorothioate 20-mer The synthesis of the above sequence was performed on a Pharmacia OligoPilot II Synthesizer on a 620 µmole scale using the cyanomethylbenzyl phosphoramidites and Pharmacia's primar support. Detritylation was performed using 3% dichloroacetic acid in dichloromethane (volume/volume). Sulfurization was performed using a 0.2 M solution of Beaucage reagent in acetonitrile: for 2 minutes. At the end of synthesis, the support was washed with acetonitrile, cleaved, deprotected and purified as described above.

EXAMPLE 12

Synthesis of Fully-Modified 5'-d(GCG-TTT-GCT-CTT-CTT-CTT-GCG)-3' Phosphorothioate 21-mer The synthesis of the above sequence was performed on a Pharmacia OligoPilot II Synthesizer on a 620 µmole scale using the cyanomethylbenzyl phosphoramidites and Pharmacia's primar support. Detritylation was performed using 3% dichloroacetic acid in dichloromethane (volume/volume). Sulfurization was performed using a 0.2 M solution of Beaucage reagent in acetonitrile: for 2 minutes. At the end of synthesis, the support was washed with acetonitrile, cleaved, deprotected and purified as described above.

EXAMPLE 13

Synthesis of Fully-Modified 5'-d(GTT-CTC-GCT-GGT-GAG-TTT-CA)-3' Phosphorothioate 20-mer The synthesis of the above sequence was performed on a Pharmacia OligoPilot II Synthesizer on a 620 µmole scale using the cyanomethyl phosphoramidites and Pharmacia's primar support. Detritylation was performed using 3% dichloroacetic acid in toluene (volume/volume). Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified as described above.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for the preparation of an oligomeric compound having a moiety of Formula I:

wherein:
 $X_4$ is Z or H;
 Z is CN, halogen, alkaryl, substituted sulfoxyl, substituted sulfonyl, or a substituted thio group, wherein said substituent is alkyl, aryl, or alkaryl; and
 $X_1$ is O or S;
comprising the steps of:
 (a) providing a compound having the Formula II:

wherein:
 each $R_1$, is, independently, H, —OH, —F, or —O—$X_3$—D;
 $X_3$ is alkylenyl having from 1 to 10 carbons;
 D is H, amino, protected amino, alkyl substituted amino, imidazolyl, or (—O—$X_3$)$_p$H where p is 1 to about 10;
 each $X_2$ is O or S;
 $R_3$ is selected from the group consisting of hydrogen, a hydroxyl protecting group, and a linker connected to a solid support;
 each B, independently, is selected from the group consisting of a naturally occurring nucleobase, a non-naturally occurring nucleobase, a protected naturally occurring nucleobase, and a protected non-naturally occurring nucleobase;
 n is 0 to about 50;
 each Q is —$X_1$H or $R_5$ is selected from the group consisting of —N($R_6$)$_2$, a heterocycloalkyl ring containing from 4 to 7 atoms, and having up to 3 heteroatoms selected from nitrogen, sulfur, and oxygen, and a heterocycloalkenyl ring containing from 4 to 7 atoms, and having up to 3 heteroatoms selected from nitrogen, sulfur, and oxygen; and $R_6$ is straight or branched chain alkyl having from 1 to 10 carbons; and (b) reacting the compound of Formula II with a compound having Formula III:

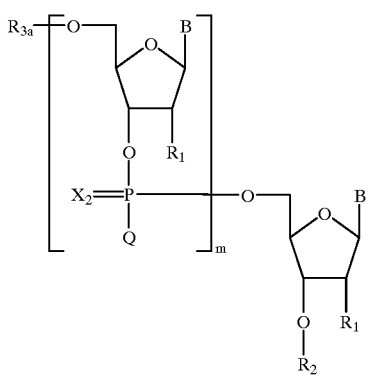

wherein $R_{3a}$ is hydrogen; and $R_2$ is a hydroxyl protecting group, or a linker connected to a solid support, provided that $R_2$ and $R_3$ are not both simultaneously a linker connected to a solid support;

to form the oligomeric compound.

2. The method of claim 1 further comprising the step of oxidizing or sulfurizing the oligomeric compound to form a further compound having Formula III, wherein $R_{3a}$ is selected from the group consisting of hydrogen, a hydroxyl protecting group, and a linker connected to a solid support; and where m is increased by n+1.

3. The method of claim 2 further comprising a capping step.

4. The method of claim 3 wherein the capping step is performed subsequent to oxidation or sulfurization.

5. The method of claim 3 wherein the capping step is performed prior to oxidation.

6. The method of claim 3 further comprising the step of cleaving the oligomeric compound to produce a compound having the Formula IV:

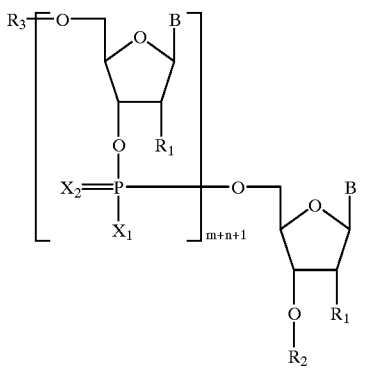

wherein $R_2$ is H.

7. The method of claim 1 wherein $X_4$ is H; and Z is CN.

8. The method of claim 7 wherein —CH($X_4$)—Z is in the ortho or para position.

9. The method of claim 8 wherein each $R_6$ is isopropyl.

10. The method of claim 8 wherein $X_2$ is O.

11. The method of claim 10 wherein $X_1$ is S.

12. The method of claim 10 wherein $X_1$ is O.

13. The method of claim 8 wherein $X_2$ is S.

14. The method of claim 13 wherein $X_1$ is S.

15. The method of claim 13 wherein $X_1$ is O.

16. The method of claim 1 wherein $X_4$ is H, —CH($X_4$)—Z is in the para position; Z is CN; $X_1$ is O; and $R_5$ is diisopropylamino.

17. The method of claim 1 wherein the compound of Formula II is obtained by reaction of a compound having Formula V:

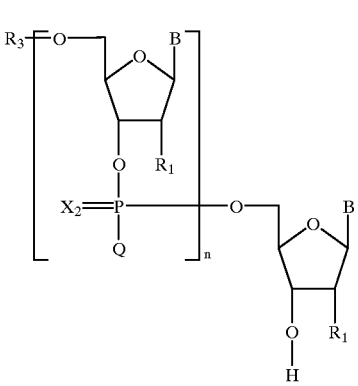

with a compound having the Formula VI:

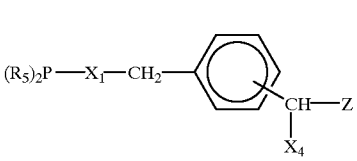

in the presence of an acid. 18. The method of claim 1 wherein the compound of Formula II is obtained by reaction of a compound having Formula V:

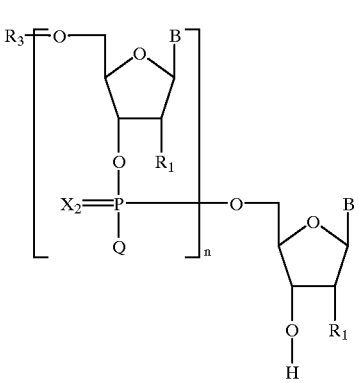

with a chlorophosphine compound of formula $ClP[i-Pr_2N]_2$, followed by reaction with a compound of Formula XX:

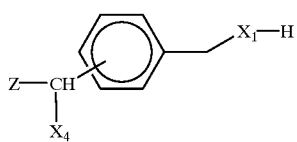

XX in the presence of an acid.

19. The method of claim 18 wherein $X_1$ is O; $X_4$ is H; and Z is CN.

20. A compound hating Formula VII:

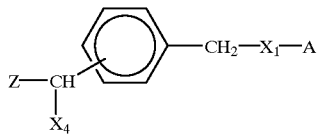

VII wherein:

$X_4$ is Z or H;

Z is CN, halogen, alkaryl, substituted sulfoxyl, substituted sulfonyl, or a substituted thio group, wherein said substituent is alkyl, aryl or alkaryl;

$X_1$ is O or S;

A is $(R_7)(R_8)P—$; and $R_8$ is $P_5$, or has the Formula VIII:

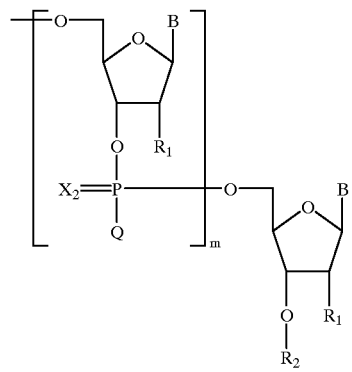

VIII wherein:

each $R_1$ is, independently, H, —OH, —F, or —O—$X_3$—D;

$X_3$ is alkylenyl having from 1 to 10 carbons;

D is H, amino, protected amino, alkyl substituted amino, imidazolyl, or $(—O—X_3)_pH$, where p is 1 to about 10;

each $X_2$ is O or S;

$R_5$ is selected from the group consisting of —N$(R_6)_2$, a heterocycloalkyl ring containing from 4 to 7 atoms, and having up to 3 heteroatoms selected from nitrogen, sulfur, and oxygen and a heterocycloalk-enyl ring containing from 4 to 7 atoms, and having up to 3 heteroatoms selected from nitrogen, sulfur, and oxygen;

each Q is —$X_1$H or

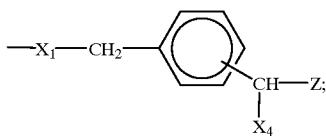

m is 0 to about 50;

each B, independently, is selected from the group consisting of a naturally occurring nucleobase, a non-naturally occurring nucleobase, a protected naturally occurring nucleobase and a non-naturally occurring nucleobase; and $R_7$ is $R_5$, or has the Formula IX:

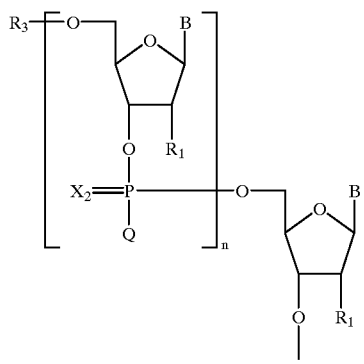

IX wherein:

$R_3$ is hydrogen, a hydroxyl protecting group, or a linker connected to a solid support; and n is 0 to about 50; with the proviso that the sum of m and n does not exceed 50 and with the proviso that both $R_7$ and $R_8$ cannot be $R_5$ simultaneously.

21. The compound of claim 20 wherein $X_4$ is H; and Z is CN.

22. The compound of claim 21 wherein —CH($X_4$)—Z is in the ortho or para position.

23. The compound of claim 22 wherein $X_1$ is O.

24. The compound of claim 22 wherein $X_1$ is S.

25. The compound of claim 22 wherein $R_5$ is —N(CH$(CH_3)_2)_2$.

26. The compound of claim 20 wherein $R_7$ has the Formula IX.

27. The compound of claim 26 wherein n is 1 to 30.

28. The compound of claim 26 wherein n is 1.

29. The compound of claim 26 wherein n is 0.

30. The compound of claim 26 wherein $X_4$ is H; Z is CN; and $X_1$ is O.

31. The compound of claim 26 wherein $X_4$ is H; Z is CN; and $X_1$ is S.

32. The compound of claim 26 wherein $X_4$ is H; Z is CN; $X_1$ is O; and each $R^6$ is isopropyl.

33. The compound of claim 26 wherein $X_4$ is H; Z is CN; $X_1$ is S; and each $R^6$ is isopropyl.

34. The compound of claim 20 having the Formula X:

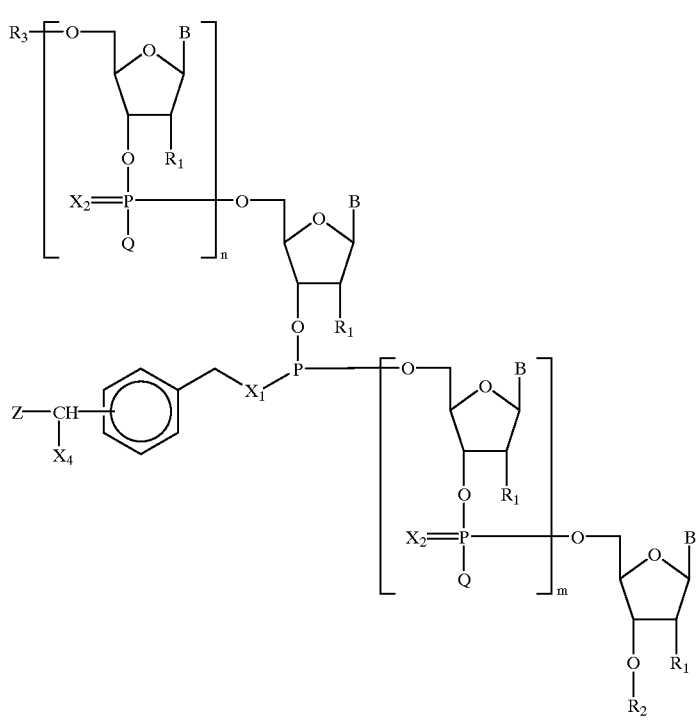

X

35. The compound of claim 34 wherein $X_4$ is H; Z is CH; and —CH($X_4$)—Z is in the ortho or para position.

36. The compound of claim 34 wherein $R_2$ is a linker connected to a solid support.

37. The compound of claim 34 wherein $R_2$ is H.

38. The compound of claim 34 wherein m and n are each 0.

39. The compound of claim 34 wherein $X_4$ is H; Z is CN; and $X_1$ is O.

40. The product produced by the process of claim 3.

41. A compound having Formula XI:

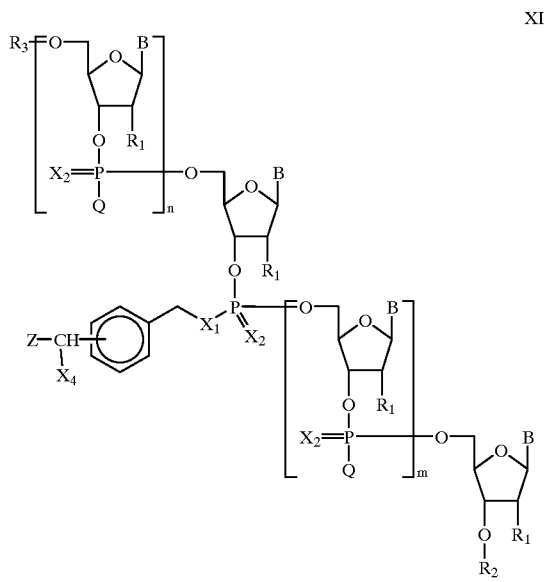

XI wherein:

each $R_1$, is, independently, H, —OH, —F, or —O—$X_3$—D;

D is H, amino, protected amino, alkyl substituted amino, imidazolyl, or (—O—$X_3$)$_p$H, where p is 1 to about 10;

$R_2$ is a hydroxyl protecting group, or a linker connected to a solid support;

$R_3$ is hydrogen, a hydroxyl protecting group, or a linker connected to a solid support, provided that $R_2$ and $R_3$ are not both simultaneously a linker connected to a solid support;

$X_1$ is O or S;

each $X_2$ is O or S;

each $X_3$ is alkylenyl having from 1 to 10 carbons;

each Q is —$X_1$H or

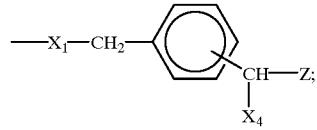

m and n are each independently an integer from 0 to about 50, provided that the sum of m and n does not exceed 50;

each B, independently, is selected from the group consisting of a naturally occurring nucleobase, a non-naturally occurring nucleobase, a protected naturally occurring nucleobase and a non-naturally occurring nucleobase;

$X_4$ is Z or H; and

Z is CN, halogen, alkaryl, substituted sulfoxyl, substituted sulfonyl, or a substituted thio group, wherein said substituent is alkyl, aryl, or alkaryl.

42. The compound of claim 41 wherein $R_2$ is a linker connected to a solid support.

43. The compound of claim 41 wherein $R_2$ is H.

44. The compound of claim 41 wherein m and n are each 0.

45. The compound of claim 41 wherein $X_4$ is H; Z is CN; and $X_1$ is O.

46. The compound of claim 22 wherein each Q has the formula:

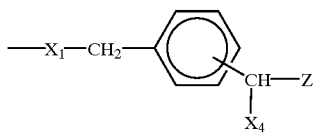

and n is from 2 to 50.

47. The compound of claim 41 wherein —CH($X_4$)—Z is in the para position.

48. An oligomeric compound comprising a moiety having Formula I:

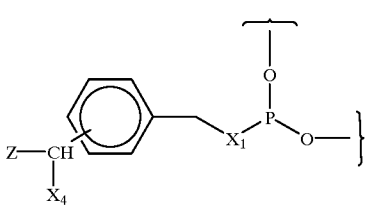

wherein:
$X_4$ is Z or H;
Z is CN, halogen, alkaryl, substituted sulfoxyl, substituted sulfonyl, or a substituted thio group, wherein said substituent is alkyl, aryl, or alkaryl; and
$X_1$ is O or S;
prepared by the steps of:
(a) providing a compound having the Formula II:

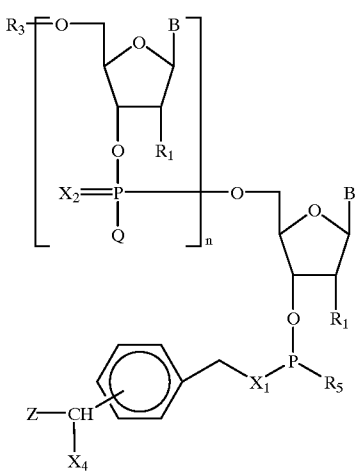

wherein:
each $R_1$, is, independently, H, —OH, —F, or —O—$X_3$—D;
$X_3$ is alkylenyl having from 1 to 10 carbons;
D is H, amino, protected amino, alkyl substituted amino, imidazolyl, or (—O—$X_3$—)$_p$H, where p is 1 to about 10;

each $X_2$ is O or S;
$R_3$ is selected from the group consisting of hydrogen, a hydroxyl protecting group, and a linker connected to a solid support;
each B, independently, is selected from the group consisting of a naturally occurring nucleobase, a non-naturally occurring nucleobase, a protected naturally occurring nucleobase and a non-naturally occurring nucleobase;
n is 0 to about 50;
each Q is —$X_1$H or

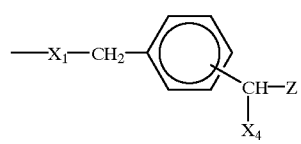

$R_5$ is selected from the group consisting of —N($R_6$)$_2$, a heterocycloalkyl ring containing from 4 to 7 atoms, and having up to 3 heteroatoms selected from nitrogen, sulfur, and oxygen and a heterocycloalkenyl ring containing from 4 to 7 atoms, and having up to 3 heteroatoms selected from nitrogen, sulfur, and oxygen; and
$R_6$ is straight or branched chain alkyl having from 1 to 10 carbons; and (b) reacting the compound of Formula II with a compound having Formula III:

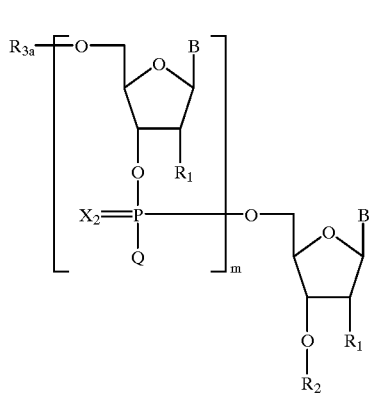

wherein $R_{3a}$ is hydrogen;
$R_2$ is a hydroxyl protecting group, or a linker connected to a solid support, provided that $R_2$ and $R_3$ are not both simultaneously a linker connected to a solid support; and (c) oxidizing the product of step (b) to form a further compound having the Formula III.

49. The compound of claim 47 wherein —CH($X_4$)—Z is in the ortho or para position.

50. A method for the preparation of a protected nucleoside phosphoramidite of formula:

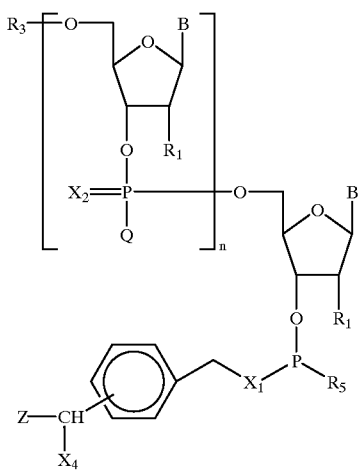

wherein:

$X_4$ is Z or H;

Z is CN, halogen, alkaryl, substituted sulfoxyl, substituted sulfonyl, or a substituted thio group, wherein said substituent is alkyl, aryl, or alkaryl;

$X_1$ is O or S;

each $R_1$, is, independently, H, —OH, —F, or —O—$X_3$—D;

$X_3$ is alkylenyl having from 1 to 10 carbons;

D is H, amino, protected amino, alkyl substituted amino, imidazolyl, or (—O—$X_3$)$_p$H, where p is 1 to about 10;

each $X_2$ is O or S;

$R_3$ is hydrogen, a hydroxyl protecting group, or a linker connected to a solid support;

each B, independently, is selected from the group consisting of a naturally occurring nucleobase, a non-naturally occurring nucleobase, a protected naturally occurring nucleobase, and a non-naturally occurring nucleobase;

n is 0 to about 50;

each Q is —$X_1$H or

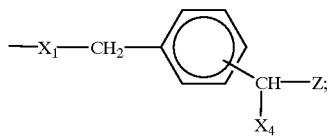

$R_5$ is selected from the group consisting of —N($R_6$)$_2$, a heterocycloalkyl ring containing from 4 to 7 atoms, and having up to 3 heteroatoms selected from nitrogen, sulfur, and oxygen and a heterocycloalkenyl ring containing from 4 to 7 atoms, and having up to 3 heteroatoms selected from nitrogen, sulfur, and oxygen; and $R_6$ is straight or branched chain alkyl having from 1 to 10 carbons;

comprising:

selecting a protected nucleoside of formula:

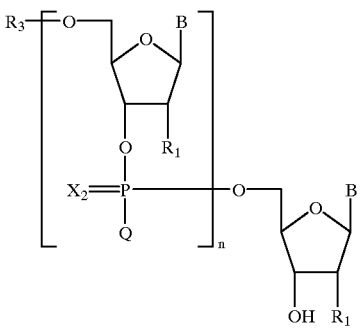

reacting the protected nucleoside with a chlorophosphine compound of formula ClP($R_5$)$_2$ in the presence of a base; and protecting the product by reaction with a compound of Formula XX:

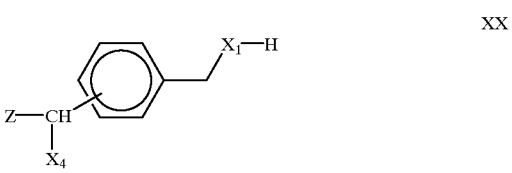

in the presence of an acid;

to form the protected nucleoside phosphoramidite.

51. The method of claim 50 wherein $X_1$ is O; $X_4$ is H; and Z is CN.

52. The method of claim 50 wherein —CH($X_4$—)—Z is in the para position.

53. The method of claim 52 wherein $X_1$ is O.

54. The method of claim 53 wherein $R_5$ is —N($R_6$)$_2$ where $R_6$ is isopropyl.

55. The method of claim 53 wherein n is 0.

56. The product of the method of claim 50.

57. The compound of claim 22 wherein n is 0.

58. The compound of claim 22 wherein n is 1.

59. A compound of Formula II:

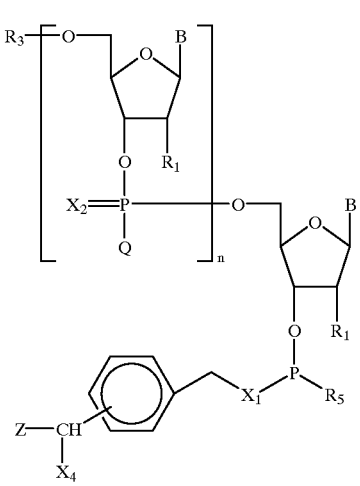

wherein:

$X_4$ is Z or H;

Z is CN, halogen, alkaryl, substituted sulfoxyl, substituted sulfonyl, or a substituted thio group, wherein said substituent is alkyl, aryl, or alkaryl;

$X_1$ is O or S;

each $R_1$, is, independently, H, —OH, —F, or —O—$X_3$—D;

$X_3$ is alkylenyl having from 1 to 10 carbons;

D is H, amino, protected amino, alkyl substituted amino, imidazolyl, or (—O—$X_3$)$_p$H where p is 1 to about 10;

each $X_2$ is O or S;

$R_3$ is selected from the group consisting of hydrogen, a hydroxyl protecting group, and a linker connected to a solid support;

each B, independently, is selected from the group consisting of a naturally occurring nucleobase, a non-naturally occurring nucleobase, a protected naturally occurring nucleobase, and a protected non-naturally occurring nucleobase;

n is 0 to about 50;

each Q is —$X_1$H or

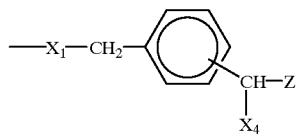

$R_5$ is selected from the group consisting of —N($R_6$)$_2$, a heterocycloalkyl ring containing from 4 to 7 atoms, and having up to 3 heteroatoms selected from nitrogen, sulfur, and oxygen, and a heterocycloalkenyl ring containing from 4 to 7 atoms, and having up to 3 heteroatoms selected from nitrogen, sulfur, and oxygen; and $R_6$ is straight or branched chain alkyl having from 1 to 10 carbons.

60. The compound of claim 59 wherein $X_4$ is H, —CH($X_4$)—Z is in the ortho or para position; Z is CN; and $X_1$ is O.

61. The compound of claim 60 wherein $R_5$ is diisopropylamino.

62. The compound of claim 61 wherein n is 0.

* * * * *

UNITED STATES PATENT AND TRADEMARK OFFICE
CERTIFICATE OF CORRECTION

PATENT NO. : 6,020,475
DATED : February 1, 2000
INVENTOR(S) : Capaldi et al.

It is certified that error appears in the above-identified patent and that said Letters Patent is hereby corrected as shown below:

Title page,
OTHER PUBLICATIONS,
In "Wright P.et al." please delete "bia phosphora;midite" and insert therefor -- via phosphoramidite --;

Column 14,
Line 23, please delete "$R_{3a}$" and insert therefor -- $R_3$ --;

Column 16,
Line 56, please delete "remainer" and insert therefor -- remainder --;

Column 21,
Line 64, please delete "disulfids" and insert therefor -- disulfides --;

Column 30,
Line 4, please delete "$N^4$-benzoyl-5-0-(4,4"dimethoxytrityl)-2" and insert therefor-- $N^4$-benzoyl-5'-0-(4,4'dimethoxytrity)-2 --;

Column 36, claim 30,
Line 58, please delete "2" and insert therefor -- Z --;

Column 37, claim 35,
Line 32, please delete "CH" and insert therefor -- CN --;

Signed and Sealed this

Sixteenth Day of April, 2002

Attest:

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.    : 6,020,475
DATED         : February 1, 2000
INVENTOR(S)   : Daniel C. Capaldi et al.

Page 1 of 1

It is certified that error appears in the above-identified patent and that said Letters Patent is hereby corrected as shown below:

<u>Title page,</u>
Item [73], Assignee, delete "Pharmeuticals" and insert -- Pharmaceuticals --.

<u>Column 35,</u>
Line 34, delete "$P_5$" and insert -- $R_5$ --.

Signed and Sealed this

Second Day of May, 2006

JON W. DUDAS
*Director of the United States Patent and Trademark Office*